United States Patent
Ozaki et al.

(10) Patent No.: US 10,146,042 B2
(45) Date of Patent: Dec. 4, 2018

(54) IMAGE PROCESSING APPARATUS, STORAGE MEDIUM, AND IMAGE PROCESSING METHOD

(71) Applicant: FUJIFILM CORPORATION, Tokyo (JP)

(72) Inventors: Ryota Ozaki, Yokohama (JP); Hideto Oda, Yokohama (JP); Noriji Kato, Yokohama (JP)

(73) Assignee: FUJIFILM CORPORATION, Tokyo (JP)

( * ) Notice: Subject to any disclaimer, the term of this patent is extended or adjusted under 35 U.S.C. 154(b) by 185 days.

(21) Appl. No.: 15/065,335

(22) Filed: Mar. 9, 2016

(65) Prior Publication Data
US 2016/0187637 A1 Jun. 30, 2016

Related U.S. Application Data

(63) Continuation of application No. PCT/JP2014/074016, filed on Sep. 11, 2014.

(30) Foreign Application Priority Data

Dec. 27, 2013 (JP) ................. 2013-271141

(51) Int. Cl.
*G02B 21/00* (2006.01)
*G01N 15/00* (2006.01)
(Continued)

(52) U.S. Cl.
CPC ....... *G02B 21/365* (2013.01); *G01N 15/1475* (2013.01); *G01N 21/27* (2013.01);
(Continued)

(58) Field of Classification Search
CPC ............ G02B 21/365; G01N 15/1475; G06K 9/00127
(Continued)

(56) References Cited

U.S. PATENT DOCUMENTS 5,911,002 A 6/1999 Mitsuyama et al.
6,151,405 A 11/2000 Douglass et al.
(Continued)

FOREIGN PATENT DOCUMENTS

CN 101184166 A 5/2008
CN 101339185 A 1/2009
(Continued)

OTHER PUBLICATIONS

Dec. 9, 2014 Search Report issued in International Application No. PCT/JP2014/074016.
(Continued)

*Primary Examiner* — Jeffrey A Williams
(74) *Attorney, Agent, or Firm* — Oliff PLC

(57) ABSTRACT

An image processing apparatus includes a detection-difficulty determination unit and a detection-parameter setting unit. The detection-difficulty determination unit calculates a degree of detection difficulty indicating a degree of difficulty in detection of a target cell contained in a specimen, based on a test object condition of the specimen. The detection-parameter setting unit sets a detection parameter for the detection of the target cell from a captured image of the specimen, based on the degree of detection difficulty.

12 Claims, 10 Drawing Sheets

(51) Int. Cl.
  *G06K 9/00* (2006.01)
  *G02B 21/36* (2006.01)
  *G01N 21/27* (2006.01)
  *G01N 15/14* (2006.01)
  *H04N 7/18* (2006.01)
  *G01N 15/10* (2006.01)

(52) U.S. Cl.
  CPC ......... *G06K 9/00127* (2013.01); *H04N 7/183* (2013.01); *G01N 2015/1006* (2013.01)

(58) Field of Classification Search
  USPC .......................................................... 348/79
  See application file for complete search history.

(56) References Cited

U.S. PATENT DOCUMENTS

| | | |
|---|---|---|
| 2003/0184730 A1 | 10/2003 | Price |
| 2009/0115892 A1 | 5/2009 | Sako et al. |
| 2009/0206234 A1* | 8/2009 | Okuda ...................... G01J 3/46 250/201.2 |
| 2013/0163844 A1 | 6/2013 | Ozaki et al. |
| 2014/0092228 A1 | 4/2014 | Usuba et al. |

FOREIGN PATENT DOCUMENTS

| | | |
|---|---|---|
| CN | 103218804 A | 7/2013 |
| JP | 2004-248619 A | 9/2004 |
| JP | 2006-317406 A | 11/2006 |
| JP | 2012-254042 A | 12/2012 |
| JP | 2013-224966 A | 10/2013 |
| WO | 2008/007725 A1 | 1/2008 |
| WO | 2012/169088 A1 | 12/2012 |

OTHER PUBLICATIONS

Ozaki, Ryota., et al., "Automatic Detection of Nucleated Red Blood Cells from Microscope Images using Cell-Hog Feature", Journal of the Japan Society of Precision Engineering, vol. 79, No. 11, (Nov. 5, 2013)., pp. 1074-1077.
Dec. 9, 2014 Written Opinion issued in International Application No. PCT/JP2014/074016.
Apr. 7, 2017 Extended Search Report issued in European Patent Application No. 14875850.1.
Jan. 25, 2018 Office Action issued in Chinese Patent Application No. 201480056915.2.

\* cited by examiner

FIG. 3

| SAMPLE ID | SPECIMEN ID | DETECTION TARGET FLAG | NUCLEUS-CANDIDATE-AREA PARAMETER | | DETERMINATION-TARGET-AREA PARAMETER | | | |
|---|---|---|---|---|---|---|---|---|
| | | | COLOR RANGE | THE NUMBER OF CONNECTED PIXELS | STEPSIZE | MAXIMUM MAGNIFICATION | MAGNIFICATION STAGE NUMBER | |
| U0001 | S0001 | T | 60 – 250 | 100 | 1 | 4 | 6 | |
| U0001 | S0002 | T | 90 – 240 | 150 | 2 | 4 | 3 | |
| U0001 | S0003 | F | 60 – 250 | 100 | 1 | 4 | 6 | |
| U0002 | S0011 | T | 90 – 240 | 150 | 2 | 4 | 3 | |

FIG. 4
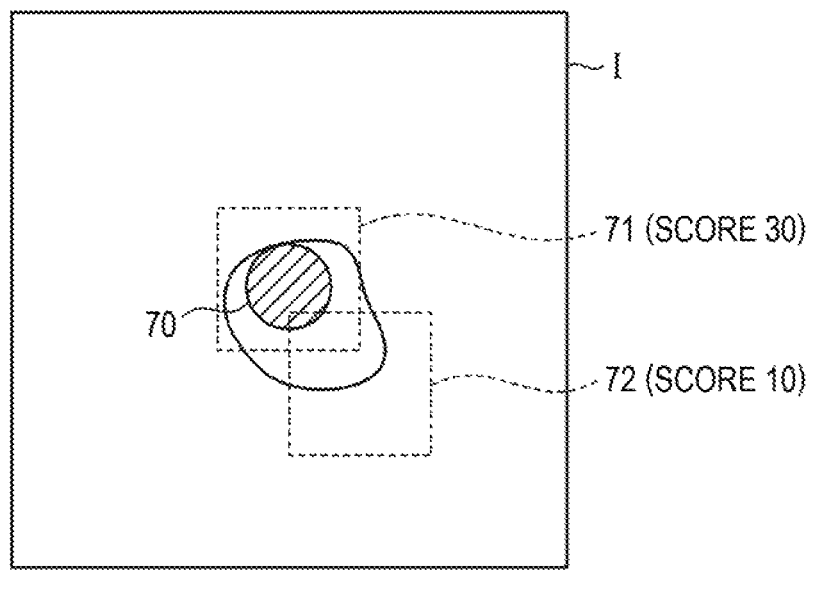
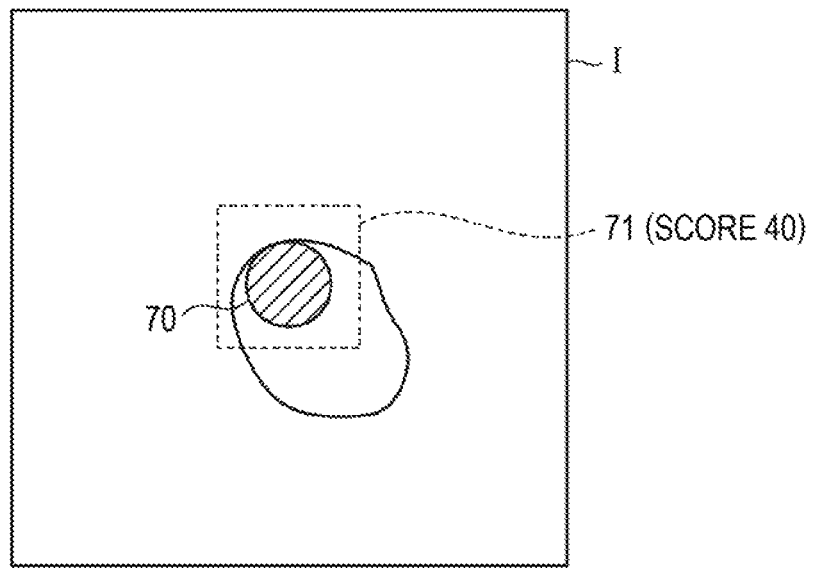

IMAGE PROCESSING APPARATUS, STORAGE MEDIUM, AND IMAGE PROCESSING METHOD

CROSS REFERENCE TO RELATED APPLICATION

This is a continuation of International Application No. PCT/JP2014/074016 filed on Sep. 11, 2014, and claims priority from Japanese Patent Application No. 2013-271141, filed on Dec. 27, 2013.

BACKGROUND

Technical Field

The present invention relates to an image processing apparatus, a storage medium, and an image processing method.

SUMMARY

An aspect of the present invention provides an image processing apparatus including a difficulty calculation unit and a setting unit. The difficulty calculation unit calculates a degree of detection difficulty indicating a degree of difficulty in detection of a target cell contained in a specimen, based on a test object condition of the specimen. The setting unit sets a detection parameter on a process of the detection of the target cell from a captured image of the specimen, based on the degree of detection difficulty.

BRIEF DESCRIPTION OF DRAWINGS

Exemplary embodiment(s) of the present invention will be described in detail based on the following figures, wherein

FIG. 3 is a diagram illustrating an exemplary detection parameter management table;

FIG. 4 is a diagram for describing an exemplary integration of target cell candidate areas;

DESCRIPTION OF EMBODIMENTS

An embodiment for implementing the present invention (hereinafter referred to as an embodiment) will be described below on the basis of the drawings.

1. Description about System Configuration

Figure 1:
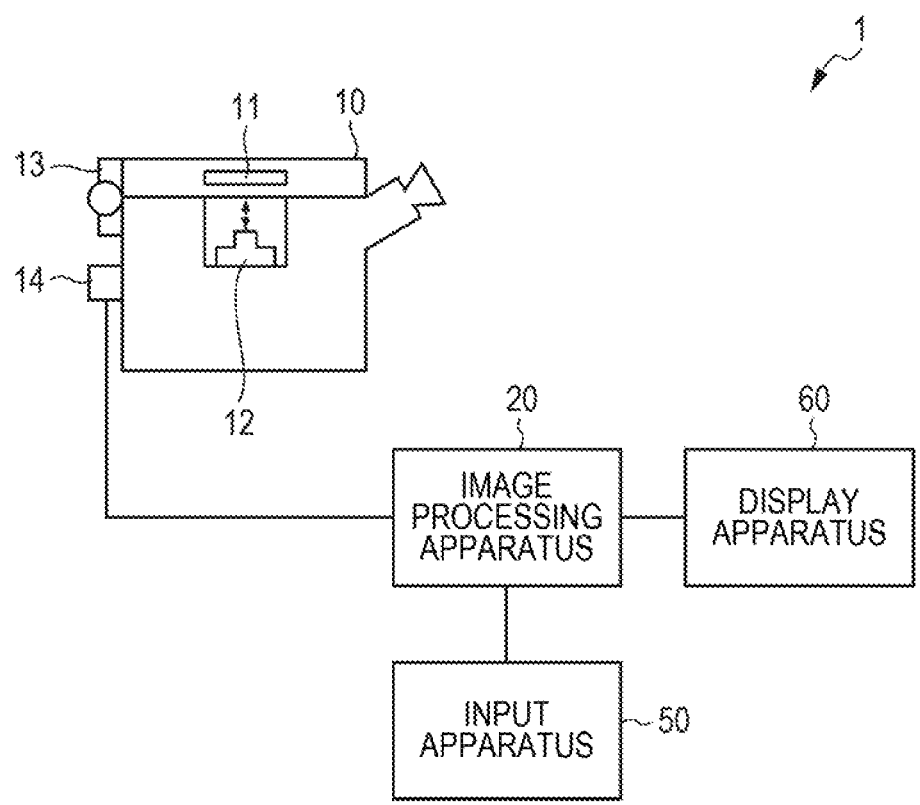
FIG. 1 is a diagram illustrating an exemplary system configuration of an image processing system according to the present embodiment.

FIG. 1 illustrates an exemplary system configuration of an image processing system 1 according to the present embodiment. As illustrated in FIG. 1, the image processing system 1 includes an optical microscope 10, an image processing apparatus 20, an input apparatus 50, and a display apparatus 60. The image processing apparatus 20 is connected to the optical microscope 10, the input apparatus 50, and the display apparatus 60 which are capable of performing data communication with the image processing apparatus 20.

The optical microscope 10 captures an image of a test object on slide glass 11 disposed on a platform, with a CCD camera 14 via an optical system such as an objective lens 12. The optical microscope 10 includes a focusing mechanism 13 which changes the distance between the slide glass 11 and the objective lens 12 so as to be capable of capturing an image of the test object on the slide glass 11 with different focal lengths. In the present embodiment, the test object is obtained by applying maternal blood to the slide glass 11 and treating it with May-Giemsa staining. Thus, fetus-derived nucleated red blood cells (NRBCs) in the maternal blood are stained bluish purple. Hereinafter, NRBCs are referred to as target cells.

The image processing apparatus 20 obtains an image captured by the optical microscope 10, and detects target cells from the captured image which is obtained. For example, the image processing apparatus 20 may determine a score (for example, a probability) indicating probability that a determination target area which is set in the image captured by the optical microscope 10 contains a target cell, on the basis of a discriminator which has learned discrimination conditions for discriminating a target cell. The process of detecting target cells, which is performed in the image processing apparatus 20, will be described in detail below.

The input apparatus 50 which is a device, such as a keyboard or a mouse, inputs an operation received from a user to the image processing apparatus 20. For example, for an image displayed on the display apparatus 60, the image processing apparatus 20 may obtain information about an image area specified by a user using the input apparatus 50, as learning information for learning positive examples and negative examples of target cells or image characteristics of other specified cells, and may cause the discriminator to learn the discrimination conditions (discrimination parameters) for discriminating a target cell, on the basis of the learning information.

The display apparatus 60 which is, for example, a liquid-crystal display apparatus 60 displays a screen on the basis of the result of a process performed by the image processing apparatus 20. For example, the display apparatus 60 displays an image captured by the optical microscope 10, and a result of detection of target cells which is performed by the image processing apparatus 20.

2. Description about Functions Provided for Image Processing Apparatus 20

Functions provided for the image processing apparatus 20 according to the present embodiment will be described.

Figure 2:
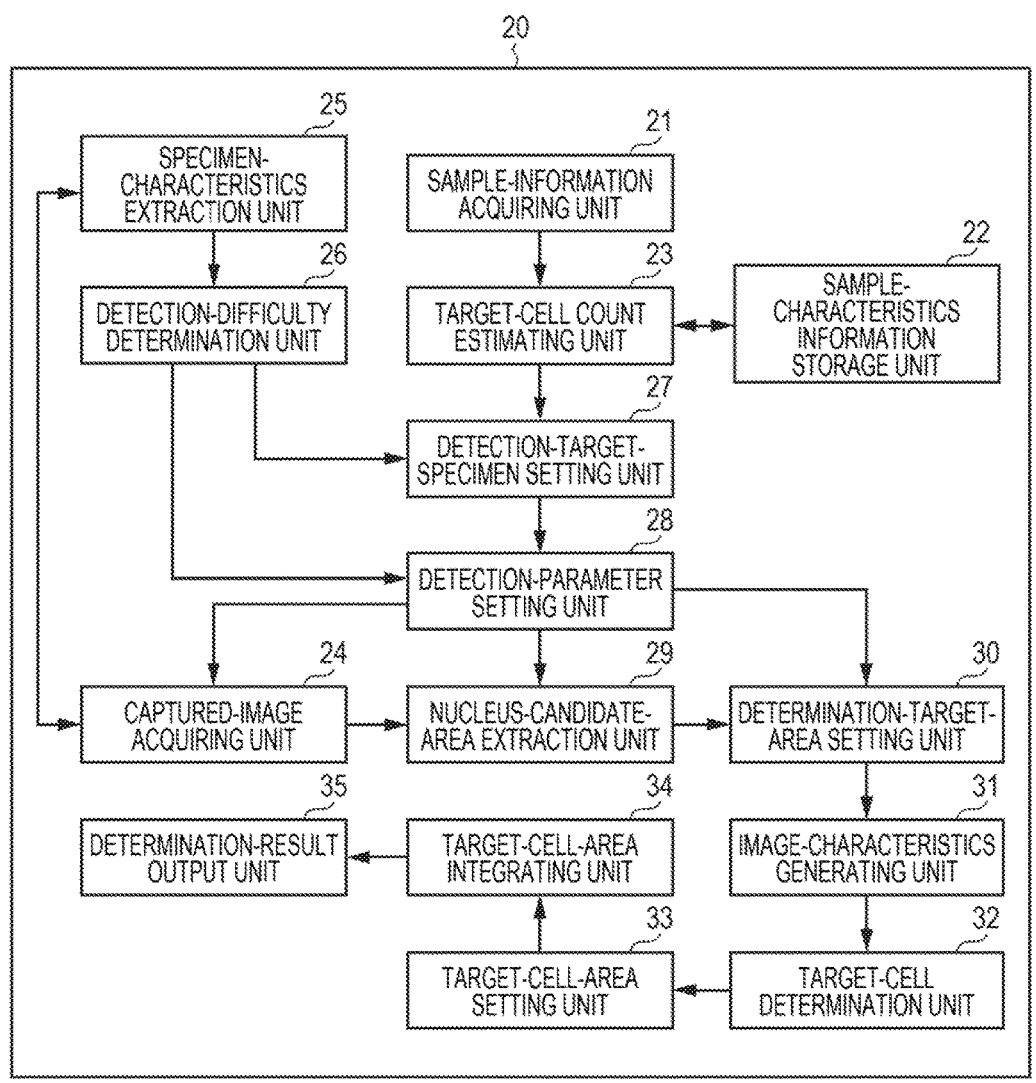
FIG. 2 is a functional block diagram illustrating exemplary functions provided for an image processing apparatus.

FIG. 2 is a functional block diagram illustrating exemplary functions provided for the image processing apparatus 20. As illustrated in FIG. 2, the image processing apparatus 20 includes a sample-information acquiring unit 21, a sample-characteristics information storage unit 22, a target-cell count estimating unit 23, a captured-image acquiring unit 24, a specimen-characteristics extraction unit 25, a detection-difficulty determination unit 26, a detection-target-specimen setting unit 27, a detection-parameter setting unit 28, a nucleus-candidate-area extraction unit 29, a determination-target-area setting unit 30, an image-characteristics generating unit 31, a target-cell determination unit 32, a target-cell-area setting unit 33, a target-cell-area integrating unit 34, and a determination-result output unit 35.

Functions of the above-described units provided for the image processing apparatus 20 may be achieved in such a manner that the image processing apparatus 20 which is a computer including control unit such as a CPU, storage unit such as a memory, input/output unit for receiving/transmitting data from/to an external device, and the like reads programs stored in a computer-readable information storage medium and executes them. The programs may be supplied to the image processing apparatus 20 through an information storage medium, such as an optical disk, a magnetic disk, a magnetic tape, a magneto-optical disk, or a flash memory, or may be supplied to the image processing apparatus 20 through a data network such as the Internet. The functions of the units provided for the image processing apparatus 20 will be described in detail below.

The sample-information acquiring unit 21 obtains information (sample information) about a sample of a test target (mother's body). For example, the sample-information acquiring unit 21 may obtain the sample information on the basis of data inputted via the input apparatus 50. For example, the sample information may include the age, the medical history weeks of pregnancy, or the like of a person (mother) from whom maternal blood as a test object has been taken.

The sample-characteristics information storage unit 22 stores information used when target cells contained in a sample are estimated on the basis of the characteristics of the sample. For example, the sample-characteristics information storage unit 22 may use classifications according to the characteristics of the sample to store, for example, the target cell count per unit blood volume for each classification. For example, the image processing apparatus 20 may generate a feature vector for each of samples on the basis of each piece of information of the age, the medical history, the number of weeks in pregnancy, and may perform clustering on the samples. The image processing apparatus 20 may store a representative value (for example, an average) of the target cell (nucleated red blood cell) count per unit blood volume which is measured in advance for the samples included in each cluster, as the representative nucleated red blood cell count in association with a corresponding one of the clusters in the sample-characteristics information storage unit 22. The sample-characteristics information storage unit 22 may store a table or a mathematical expression which defines a relationship between information about the age, the medical history, and the number of weeks in pregnancy, and the nucleated red blood cell count corresponding to the information.

The target-cell count estimating unit 23 estimates the target cell count contained in the sample obtained by the sample-information acquiring unit 21, on the basis of the sample information about the sample (information representing characteristics of the sample) and the information stored in the sample-characteristics information storage unit 22. For example, the target-cell count estimating unit 23 estimates the target cell count contained in a test object (maternal blood) obtained from the sample, on the basis of the representative target cell count stored in the sample-characteristics information storage unit 22 in association with the classification corresponding to the sample information obtained by the sample-information acquiring unit 21. For example, the target-cell count estimating unit 23 may obtain the estimated target cell count by multiplying the blood volume of the test object by the nucleated red blood cell count per unit blood volume stored in the sample-characteristics information storage unit 22 in association with the classification corresponding to the sample information obtained by the sample-information acquiring unit 21.

The method of estimating the target cell count is not limited to the above-described method. For example, for each of one or more samples, the sample-characteristics information storage unit 22 may store a feature vector of the sample and the target cell count of the sample in advance in such a manner that the feature vector is associated with the target cell count. The target-cell count estimating unit 23 may specify a feature vector similar to that of the target sample (for example, the closest feature vector) from the feature vectors of the samples stored in the sample-characteristics information storage unit 22, and the target cell count which is associated with the specified feature vector may be used as the target cell count for the target sample.

The captured-image acquiring unit 24 obtains a captured image obtained by capturing an image of the test object (maternal blood) which is obtained from a sample and which is put on the slide glass. For example, the captured-image acquiring unit 24 obtains a captured image obtained by capturing an image of the test object (maternal blood) with a CCD camera 14 provided for an optical microscope 10, from the optical microscope 10. On the basis of detection parameters described below, when a detection target flag of the target test object is set to true (T), the captured-image acquiring unit 24 may obtain a captured image. When the detection target flag of the target test object is set to false (F), the captured-image acquiring unit 24 may obtain no captured images.

The specimen-characteristics extraction unit 25 extracts characteristics of a target specimen. The characteristics of a specimen include information representing specimen test object conditions. For example, the specimen-characteristics extraction unit 25 may extract evenness of the thickness of a specimen generated from a sample, the staining degree of cell nuclei, the content percentage of white blood cells, and the like as the specimen characteristics. The specimen-characteristics extraction unit 25 may extract the specimen characteristics for each of all or some (for example, those limited to specimens to be subjected to the detection) of specimens generated from the target sample.

For example, the specimen-characteristics extraction unit 25 may measure the depths from the surface of a specimen to the slide glass at multiple points of the specimen by using the optical microscope 10, and may calculate the evenness (A) of the thickness of the specimen as the inverse of the variance of the multiple depths obtained through the measurement.

For example, the specimen-characteristics extraction unit 25 may calculate the staining degree (B) of cell nuclei in a specimen as a value obtained by dividing a predetermined threshold by the average brightness value of a captured image (which may be captured by using the optical microscope 10) of the specimen (that is, threshold/average brightness value), or may calculate the staining degree (B) as a ratio of pixels having a brightness value lower than a predetermined threshold in a captured image of the specimen.

For example, the specimen-characteristics extraction unit 25 may calculate the content percentage (C) of white blood cells in a specimen as a ratio of pixels whose color is lighter than a predetermined density, in a captured image (which may be captured by using the optical microscope 10) of the specimen.

The detection-difficulty determination unit 26 determines the degree of difficulty (Df) in detection of target cells from a specimen, on the basis of the specimen characteristics extracted by the specimen-characteristics extraction unit 25. For example, the detection-difficulty determination unit 26 may calculate the degree of detection difficulty Df for a specimen by using the following equation (1) on the basis of the evenness A of the thickness of the specimen, the staining degree B of cell nuclei in the specimen, and the content percentage C of white blood cells in the specimen which are extracted by the specimen-characteristics extraction unit 25. The symbols w1, w2, and w3 may represent predetermined coefficients, each of which is equal to or more than 0 and which satisfy the equation w1+w2+w3=1. The symbol A0 may represent a reference value of the evenness of the specimen thickness. The symbol B0 may represent a reference value of the staining degree of cell nuclei in the specimen. The symbol C0 may represent a reference value of the content percentage of white blood cells in the specimen.

$$Df = w1 \cdot A0/A + w2 \cdot B0/B + w3 \cdot C/C0 \tag{1}$$

According to the above-described expression (1), the calculated degree of detection difficulty Df becomes lower as the evenness A of the thickness of a specimen becomes larger. The calculated degree of detection difficulty Df becomes lower as the staining degree B of cell nuclei in the specimen becomes larger. The calculated degree of detection difficulty Df becomes higher as the content percentage C of white blood cells in the specimen becomes larger. The detection-difficulty determination unit 26 may change the degree of detection difficulty Df calculated by using the above-described expression (1) to a value from 0 to 1. For example, the detection-difficulty determination unit 26 may set Df to 0 when Df is lower than the lower threshold limit. The detection-difficulty determination unit 26 may set Df to 1 when Df is larger than the upper threshold limit (for example, a value larger than 1).

The detection-target-specimen setting unit 27 sets specimens which are to be subjected to the detection, from multiple specimens generated from the target sample, on the basis of at least one of the estimated target cell count (Cb) estimated by the target-cell count estimating unit 23 and the degree of detection difficulty (Df) determined by the detection-difficulty determination unit 26.

For example, the detection-target-specimen setting unit 27 calculates the target cell count per one specimen (a=Cb/N) by dividing the estimated target cell count (Cb) estimated for the target sample by the number (N) of specimens generated from the test object. For the necessary target cell count (Z), when Cb>Z, the detection-target-specimen setting unit 27 may determine the number of specimens which are to be subjected to the detection, to be set at an integer X which satisfies the expression a·X≥Z. When Cb≤Z, the detection-target-specimen setting unit 27 may determine the number of specimens which are to be subjected to the detection, to be set at N (the number of all specimens). The detection-target-specimen setting unit 27 may select specimens (for example, in order of identification number or in order of create date and time), the number of which is equal to the number of specimens to be subjected to the detection, from the N specimens generated from the test object, and may set the detection target flags of the selected specimens to true (T) and set those of the unselected specimens to false (F).

When specimens to be subjected to the detection are to be set on the basis of the degree of detection difficulty calculated by the detection-difficulty determination unit 26, for example, the detection-target-specimen setting unit 27 may set specimens having the degree of detection difficulty which is lower than a threshold, among multiple specimens generated from the target sample, as specimens to be subjected to the detection.

The detection-parameter setting unit 28 sets detection parameter sets used when a detection process is to be performed on specimens generated from the test object. For example, the detection-parameter setting unit 28 sets a detection parameter set on the basis of at least one of a specimen which is to be subjected to the detection and which is set by the detection-target-specimen setting unit 27, and the degree of detection difficulty determined by the detection-difficulty determination unit 26. For example, a detection parameter set may include the detection target flag indicating whether or not the specimen is to be subjected to the detection, nucleus-candidate-area parameters indicating a condition of an image area to be extracted as a nucleus candidate area from a captured image of the specimen, and determination-target-area parameters indicating a setting condition of setting determination target areas for a captured image of the specimen.

FIG. 3 illustrates an exemplary detection parameter management table which stores detection parameter sets which are set by the detection-parameter setting unit 28. As illustrated in FIG. 3, the detection parameter management table stores a sample ID for identifying a sample, a specimen ID for identifying each of multiple specimens obtained from the sample, a detection target flag indicating whether or not the specimen is to be subjected to the detection, nucleus-candidate-area parameters, and determination-target-area parameters in such a manner that these pieces of information are associated with each other. The nucleus-candidate-area parameters include a color range of target pixels to be extracted as a nucleus candidate area, and a threshold of the number of connected pixels. The determination-target-area parameters include a stepsize indicating the shift amount between pixels used as the base points of determination target areas for the nucleus candidate area, a maximum magnification indicating a size ratio between the smallest determination target area and the largest determination target area among determination target areas which have different sizes and which are set by using pixels used as the base points of the determination target areas, and a magnification stage number which indicates how many stages of magnification are to be performed when areas from the smallest determination target area to the largest determination target area are to be generated.

For example, the detection-parameter setting unit 28 may set a detection parameter set on the basis of at least one of the degree of detection difficulty Df determined by the detection-difficulty determination unit 26 and a margin Y (Y=a·X−Z) which is the difference between the necessary target cell count Z and the product of the target cell count a per specimen and the number X of specimens which are to be subjected to the detection and which are set by the detection-target-specimen setting unit 27. More specifically, the detection-parameter setting unit 28 may predetermine a detection parameter set for each of stage levels L1 to LM whose number is equal to M which is an integer equal to or larger than 2 (for the same image, the number of nucleus candidate areas and the number of determination target areas for the level Li+1 which are extracted/set by using a detection parameter set are more than those for the level Li), may determine a level on the basis of at least one value of the margin Y and the degree of detection difficulty Df, and may set a detection parameter set on the basis of the determined level. For example, the detection-parameter setting unit 28 may predetermine the range of the margin for each of the M stage levels, and may determine a level on the basis of determination as to which level has a range including the calculated margin Y. In addition, for example, the detection-parameter setting unit 28 may predetermine the range of the degree of detection difficulty for each of the M stage levels, and may determine a level on the basis of determination as to which level has a range including the calculated degree of detection difficulty Df. Further, for example, the detection-parameter setting unit 28 may predetermine the range of the sum of the margin and the degree of detection difficulty for each of the M stage levels, and may determine a level on the basis of determination as to which level has a range including the sum of the calculated value Y and the degree Df.

For each of the specimens which are set by the detection-target-specimen setting unit 27, the detection-parameter setting unit 28 may set a different detection parameter set on the basis of the degree of detection difficulty which is calculated for the specimen.

For a specimen to be processed, the nucleus-candidate-area extraction unit 29 extracts nucleus candidate areas on the basis of the nucleus-candidate-area parameters which are set by the detection-parameter setting unit 28 for the specimen, from the captured image obtained by the captured-image acquiring unit 24 for the specimen. For example, the nucleus-candidate-area extraction unit 29 may perform binarization so as to convert a pixel included in the color range in the nucleus-candidate-area parameters into a black pixel and convert a pixel which is not included in the color range into a white pixel, and may extract, as nucleus candidate areas, connected pixel groups, the number of which is larger than that of connected pixels which is included in the nucleus-candidate-area parameters, from connected pixel groups obtained by connecting adjacent black pixels.

For the captured image obtained by the captured-image acquiring unit 24 for a specimen to be processed, the determination-target-area setting unit 30 sets determination target areas on which determination as to whether or not target cells are present is to made, on the basis of a nucleus candidate area extracted by the nucleus-candidate-area extraction unit 29 and the determination-target-area parameters which are set by the detection-parameter setting unit 28 for the specimen. For example, for each of one or more pixels included in a nucleus candidate area extracted by the nucleus-candidate-area extraction unit 29, the determination-target-area setting unit 30 sets a rectangular area in which the pixel is present at the center (or the base point), as a determination target area. On the basis of the stepsize (shift amount) included in the determination-target-area parameters which are set for a specimen to be processed, the determination-target-area setting unit 30 may sequentially set determination target areas by moving the pixel which is present in the nucleus candidate area and which serves as the base point of a determination target area, by the stepsize step by step. In addition, on the basis of the maximum magnification and the magnification stage number included in the determination-target-area parameters which are set for a specimen to be processed, the determination-target-area setting unit 30 may set determination target areas having different sizes by using one pixel which serves as the base point of a determination target area and by changing the size of the determination target area from 1× to the maximum magnification multiple times, as many as the number of stages predetermined as the magnification stage number.

The image-characteristics generating unit 31 generates an image feature value for a determination target area which is set by the determination-target-area setting unit 30. For example, the image-characteristics generating unit 31 may calculate an HOG feature value of a determination target area, and may use the HOG feature value as an image feature value. Processes of calculating two types of HOG feature values will be specifically described below.

The image-characteristics generating unit 31 obtains the luminance gradient direction and the luminance gradient intensity for each pixel in a determination target area. The image-characteristics generating unit 31 divides the target image into blocks, the number of which is Y and each of which is constituted by cells whose number is X. The image-characteristics generating unit 31 obtains a luminance gradient direction histogram ([a first gradient direction value, a second gradient direction value, . . . , a ninth gradient direction value]) from the luminance gradient directions and the luminance gradient intensities for each of the cells included in a corresponding one of the blocks, and performs normalization for each of the blocks so that the mean square of the gradient direction values is equal to 1. The image-characteristics generating unit 31 uses, as a feature value of a block, the values, the number of which is equal to X×9 and which are obtained by combining the normalized luminance gradient direction histograms in the block, and further uses, as the HOG feature value of the determination target area, the values, the number of which is equal to Y×X×9 and which are obtained by combining all of the blocks in the target image.

Instead, the image-characteristics generating unit 31 obtains the luminance gradient direction and the luminance gradient intensity for each pixel in a determination target area. The image-characteristics generating unit 31 divides the target image into blocks, the number of which is Y and each of which is constituted by cells, the number of which is X. The image-characteristics generating unit 31 obtains a luminance gradient direction histogram ([a first gradient direction value, a second gradient direction value, . . . , an eighteenth gradient direction value]) from the luminance gradient directions and the luminance gradient intensities for each of the cells included in a corresponding one of the blocks. The image-characteristics generating unit 31 uses, as a feature value of a block, the values, the number of which is equal to X×18 and which are obtained by combining the luminance gradient direction histograms in the block, and further uses, as the Cell-HOG feature value of the determination target area, the values, the number of which is equal to Y×X×18 and which are obtained by combining all of the blocks in the target image.

The target-cell determination unit 32 determines a probability (the degree of confidence) that the determination target area contains a target cell, on the basis of the image feature value of a determination target area. For example, on the basis of the image feature values of image areas in which target cells are shown, the discriminator may be made to learn discrimination conditions (discrimination parameters) for a target cell in advance, and a discrimination result for the image feature value of a determination target area may be obtained by using the discriminator. The discriminator may use AdaBoost, SVM (support vector machine), or the like. The discriminator outputs a score (the degree of confidence) indicating probability that the determination target area contains a target cell, on the basis of the image feature value of the determination target area. For example, the discriminator may output a positive value score when a cell contained in the determination target area is a target cell, and may output a negative value score when the cell is not a target cell.

The target-cell-area setting unit 33 sets a candidate area (target cell area) containing a target cell, on the basis of a result of determination on a determination target area which is obtained by the target-cell determination unit 32. For example, the target-cell-area setting unit 33 may set a determination target area among the determination target areas as a candidate area for a target cell when the degree of confidence for the determination target area which is output from the discriminator is equal to or larger than 0.

The target-cell-area integrating unit 34 integrates candidate areas which are set by the target-cell-area setting unit 33 and which overlap or match each other, into one area. For example, when multiple candidate areas overlap each other, the target-cell-area integrating unit 34 may integrate the multiple candidate areas into one of the multiple candidate areas (for example, an area whose degree of confidence is the largest). The target-cell-area integrating unit 34 may determine that the multiple candidate areas overlap each other, if the multiple candidate areas are the determination target areas which are set from the same nucleus candidate area. Alternatively, the target-cell-area integrating unit 34 may determine that the multiple candidate areas overlap each other, if the multiple candidate areas overlap each other in such a manner that each of the overlapping areas is equal to or larger than a predetermined threshold. After integration, the target-cell-area integrating unit 34 may leave only a candidate area having the highest degree of confidence, or may use an area including all of the candidate areas overlapping each other, as a candidate area after integration. The target-cell-area integrating unit 34 may add the degrees of confidence of the integrated candidate areas to that of the candidate area after integration, or may use a value obtained by multiplying the degree of confidence of the candidate area after integration by the number of candidate areas overlapping each other, as the degree of confidence of the candidate area after integration.

FIG. 4 illustrates a diagram for describing an exemplary integration of target cell candidate areas. As illustrated in FIG. 4, a captured image I includes a nucleus candidate area 70, and two target cell areas 71 and 72 which overlap each other are set for the nucleus candidate area 70. The target cell area 71 has a score of 30, and the target cell area 72 has a score of 10. The target-cell-area integrating unit 34 may integrate the target cell area 72 into the target cell area 71 having the largest score among the target cell areas 71 and 72, and may add the score of the target cell area 72 to that of the target cell area 71 so as to update the score of the target cell area 71.

The determination-result output unit 35 outputs information about the candidate areas obtained through integration performed by the target-cell-area integrating unit 34, as a result of detection of target cells for the test object. For example, the determination-result output unit 35 may display a display screen on which candidate areas obtained through integration performed by the target-cell-area integrating unit 34 are displayed as a list in such a manner that the candidate areas are sorted according to their degrees of confidence, on the display apparatus 60. The determination-result output unit 35 may exclude candidate areas whose degree of confidence is less than a specified or predetermined threshold, from the list.

3. Exemplary Process

On the basis of FIGS. 5 to 10, an exemplary process performed in the image processing system 1 according to the present embodiment will be described in detail below.

3-1. First Example

On the basis of the flowcharts illustrated in FIGS. 5 to 8, a process according to a first example which is performed by the image processing system 1 will be described in detail.

3-1-1 (1). Main Process (1)

Figure 5:
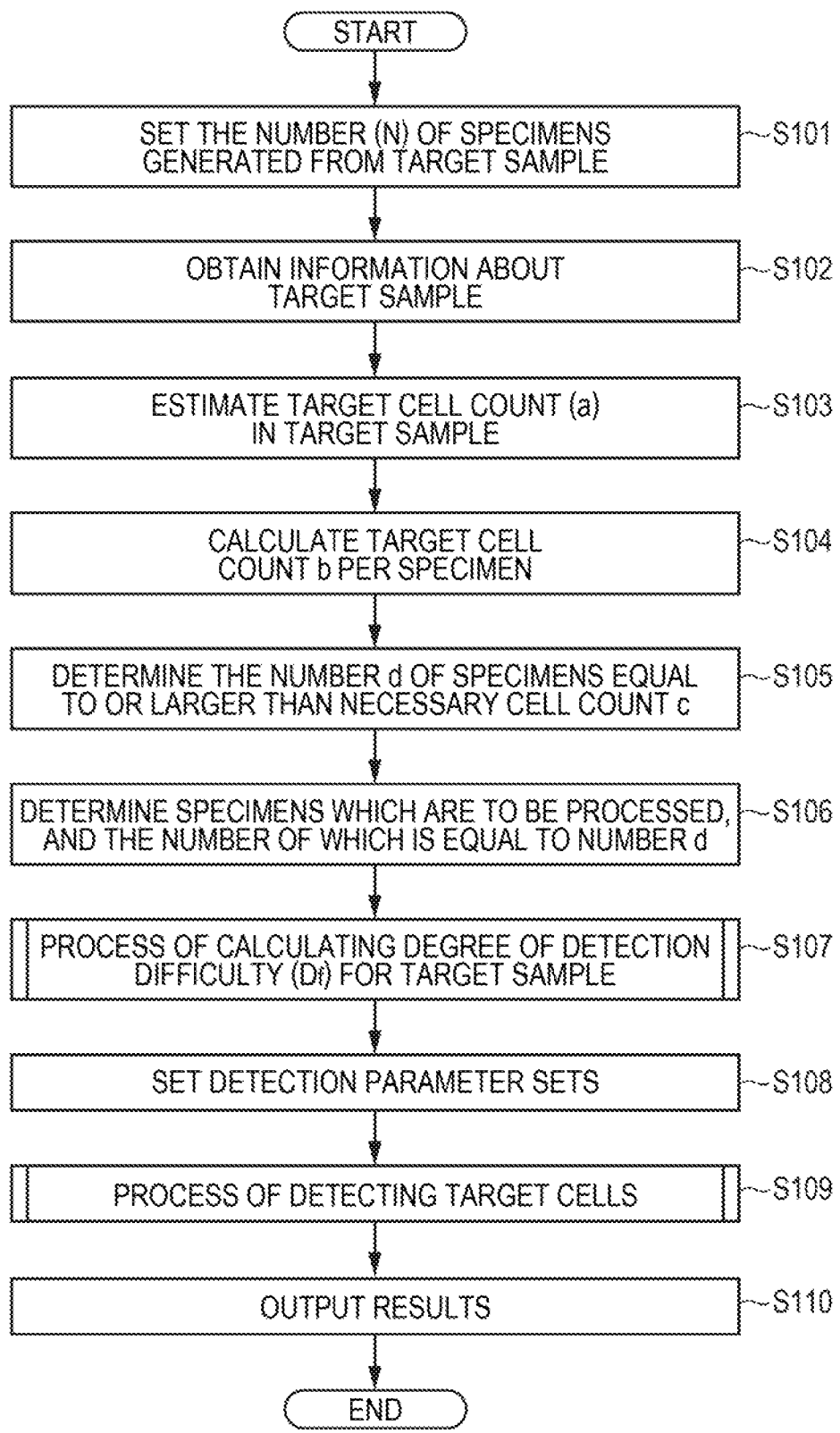
FIG. 5 is a flowchart of a process according to a first example.

As illustrated in FIG. 5, on the basis of data which is input from the input apparatus 50, the image processing apparatus 20 sets the number (N: N is an integer equal to or larger than 1) of specimens generated from a target sample (S101), and obtains information (sample information) about the target sample (S102). The sample information may include at least one of the age, the medical history, and the number of weeks in pregnancy.

The image processing apparatus 20 estimates the target cell count (a) in the target sample on the basis of the sample information obtained in S102 (S103). For example, the image processing apparatus 20 may specify a classification to which the sample information obtained in S102 belongs, and may calculate the estimated target cell count in the sample on the basis of the representative target cell count (reference target cell count) per unit blood which is predetermined for the specified classification and the blood volume of the test object, i.e., the sample.

The image processing apparatus 20 calculates the target cell count (b) per specimen on the basis of the target cell count (a) calculated in S103 and the number (N) of specimens which is set in S101 (S104). The image processing apparatus 20 determines the number (d) of specimens which are to be subjected to the detection and which contain a cell count which is equal to or larger than the necessary cell count (c) necessary for the detection, on the basis of the target cell count (b) per specimen which is calculated in S104 (S105).

The image processing apparatus 20 selects and determines specimens, which are to be processed and the number of which is equal to the number (d), which is determined in S105, of specimens to be subjected to the detection, from the multiple specimens generated from the target sample (S106).

The image processing apparatus 20 performs a process of calculating the degree of detection difficulty which indicates the degree of difficulty in detection of target cells from a specimen which is to be processed and which is determined in S106 (S107). The process of calculating the degrees of detection difficulty will be described in detail on the basis of the flowchart in FIG. 6.

3-1-2. Process of Calculating the Degrees of Detection Difficulty

Figure 6:
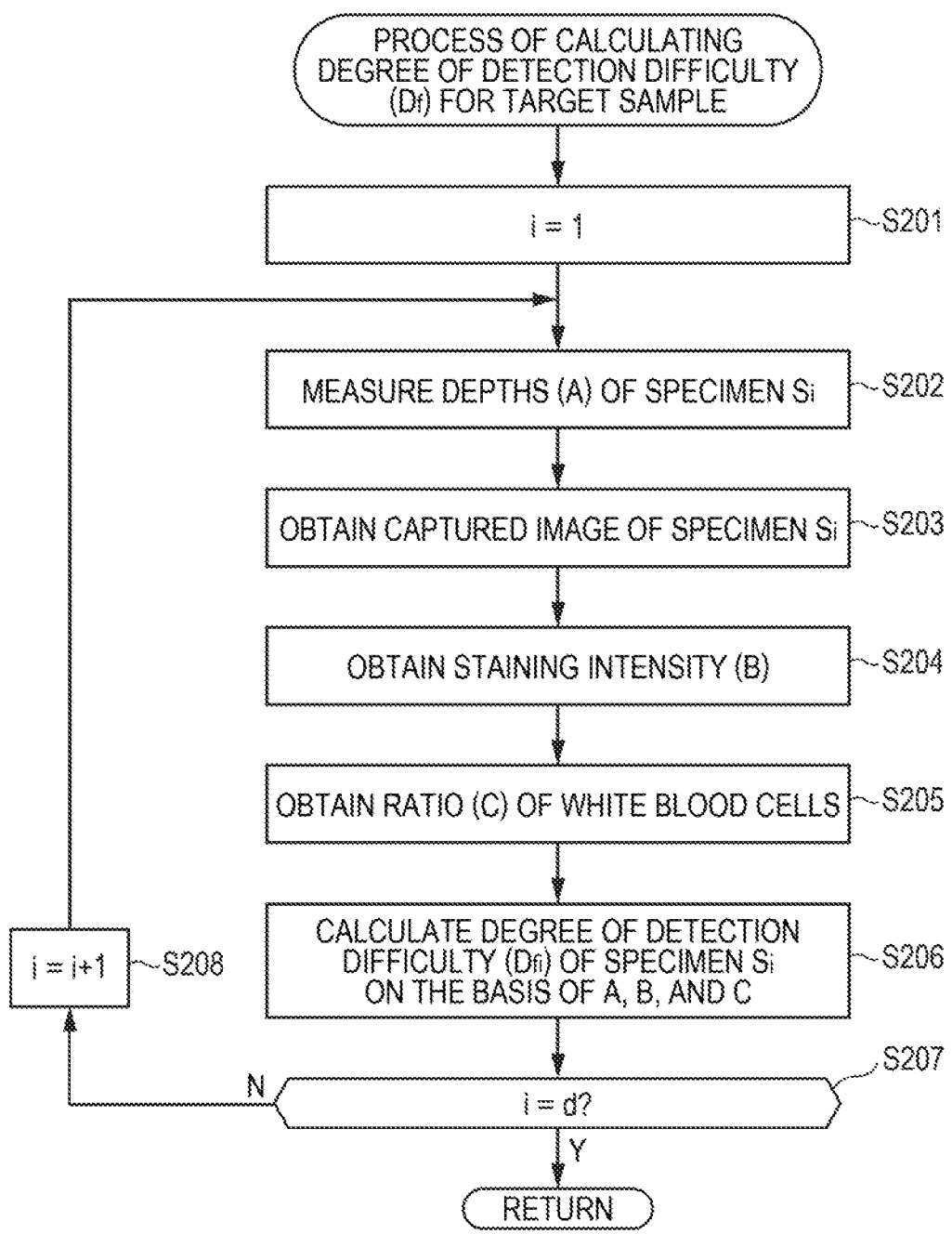
FIG. 6 is a flowchart of a process of calculating the degree of detection difficulty.

As illustrated in FIG. 6, the image processing apparatus 20 initializes a variable i to 1 (S201), and measures depths (A) of a specimen Si (S202). For example, for each of multiple points of the specimen Si, a depth from the surface of the specimen Si to the slide glass may be measured by using the optical microscope 10.

The image processing apparatus 20 obtains a captured image by capturing an image of the specimen Si by using the optical microscope 10 (S203), and obtains the staining intensity (B) of the specimen Si on the basis of the captured image which is obtained (S204). For example, the image processing apparatus 20 may calculate the staining degree (B) of cell nuclei in the specimen Si by dividing a predetermined threshold by the average brightness value of the captured image of the specimen Si (that is, threshold/average brightness value), or by calculating a ratio of pixels having a brightness value lower than a predetermined threshold in the captured image of the specimen Si.

The image processing apparatus 20 obtains the ratio (C) of white blood cells in the specimen Si on the basis of the captured image obtained in S203 (S205). For example, the image processing apparatus 20 may calculate the ratio (C) of white blood cells in the specimen Si, as a ratio of pixels having a color lighter than a predetermined density in the captured image of the specimen Si.

The image processing apparatus 20 calculates the degree of detection difficulty Df (Dfi) in detection of target cells from the specimen Si, for example, by using the above-described expression (1) on the basis of the variance of the depths (A), the staining intensity (B) of the test object, and the ratio (C) of white blood cells (S206).

If the variable i does not reach d (S207: N), the image processing apparatus 20 increments (adds 1 to) the variable i (S208), and returns the process back to S202. If the variable i reaches d (S207: Y), the image processing apparatus 20 causes the process to return. Back to the flowchart in FIG. 5, the description will be continued.

3-1-1 (2). Main Process (2)

As illustrated in FIG. 5, when the image processing apparatus 20 completes the calculation of the degrees of detection difficulty Df in detection of target cells in the specimens to be processed, the image processing apparatus 20 sets a detection parameter set on the basis of at least one of the degree of detection difficulty Df calculated in S107 and information about a specimen which is to be processed and which is determined in S106 (S108). For example, the detection parameter set may include the detection target flag indicating whether or not the specimen is to be subjected to the detection, the nucleus-candidate-area parameters indicating a condition of an image area to be extracted as a nucleus candidate area from the specimen, and the determination-target-area parameters indicating a condition of setting determination target areas for an image of the specimen. For example, the image processing apparatus 20 may set the detection target flag on the basis of information about a specimen which is to be processed and which is determined in S106, and may set the nucleus-candidate-area parameters and the determination-target-area parameters on the basis of the degree of detection difficulty Dfi calculated for the specimen Si.

The image processing apparatus 20 performs a process of detecting target cells from the sample on the basis of the detection parameter sets which are set in S108 (S109). The process of detecting target cells will be described in detail on the basis of the flowchart in FIG. 7.

3-1-3. Process of Detecting Target Cells

Figure 7:
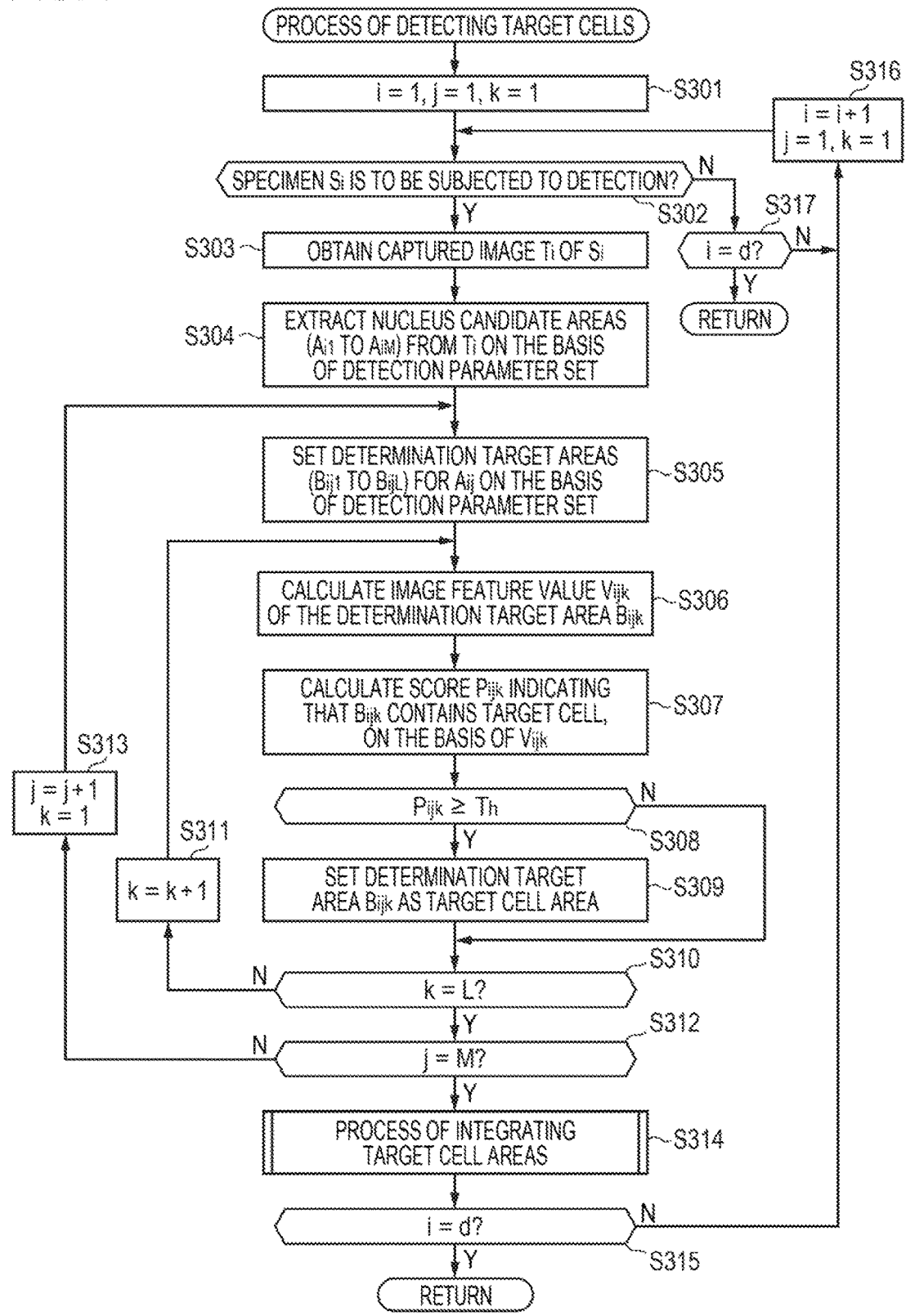
FIG. 7 is a flowchart of a process of detecting target cells.

As illustrated in FIG. 7, the image processing apparatus 20 initializes each of variables i, j, and k to 1 (S301), and determines whether or not the specimen Si of the target sample is to be subjected to the detection (S302). For example, if the detection target flag of the specimen Si is true (T), the image processing apparatus 20 determines that the specimen Si is to be subjected to the detection. If the detection target flag is false (F), the image processing apparatus 20 determines that the specimen Si is not to be subjected to the detection.

If the specimen Si is to be subjected to the detection (S302: Y), the image processing apparatus 20 causes, for example, the optical microscope 10 to capture an image of the specimen Si so as to obtain a captured image Ti of the specimen Si (S303).

The image processing apparatus 20 extracts nucleus candidate areas (Ai1 to AiM) from the captured image Ti on the basis of the nucleus-candidate-area parameters included in the detection parameter set which is set for the specimen Si (S304), where M is the number of nucleus candidate areas contained in the captured image Ti. The extraction of the nucleus candidate areas may be performed by the above-described nucleus-candidate-area extraction unit 29.

The image processing apparatus 20 sets determination target areas (Bij1 to BijL) for the nucleus candidate area Aij extracted from the captured image Ti on the basis of the determination-target-area parameters included in the detection parameter set which is set for the specimen Si (S305), where L is the number of determination target areas which are set for the nucleus candidate area Aij. The determination target areas may be set by the above-described determination-target-area setting unit 30.

The image processing apparatus 20 calculates an image feature value Vijk of the determination target area Bijk (S306). The calculation of an image feature value may be performed by the above-described image-characteristics generating unit 31.

The image processing apparatus 20 calculates a score Pijk indicating probability that the determination target area Bijk contains a target cell, on the basis of the image feature value Vijk calculated in S306 (S307).

If the score Pijk calculated in S307 is equal to or larger than a threshold Th (S308: Y), the image processing apparatus 20 sets the determination target area Bijk as a target cell area (S309).

After S309 or if the score Pijk calculated in S307 is less than the threshold Th (S308: N), the image processing apparatus 20 determines whether or not the variable k reaches L (S310). If the variable k does not reach L (S310: N), the image processing apparatus 20 increments k (adds 1 to k) (S311), and returns the process back to S306. If the variable k reaches L in S310 (S310: Y), the image processing apparatus 20 determines whether or not the variable j reaches M (S312).

If the variable j does not reach M in S312 (S312: N), the image processing apparatus 20 increments j (adds 1 to j) and initializes k to 1 (S313), and returns the process back to S305. If the variable j reaches M in S312 (S312: Y), the image processing apparatus 20 performs a process of integrating target cell areas which are set for the specimen Si (S314). The process of integrating target cell areas will be described in detail on the basis of the flowchart in FIG. 8.

3-1-4. Process of Integrating Target Cell Areas

Figure 8:
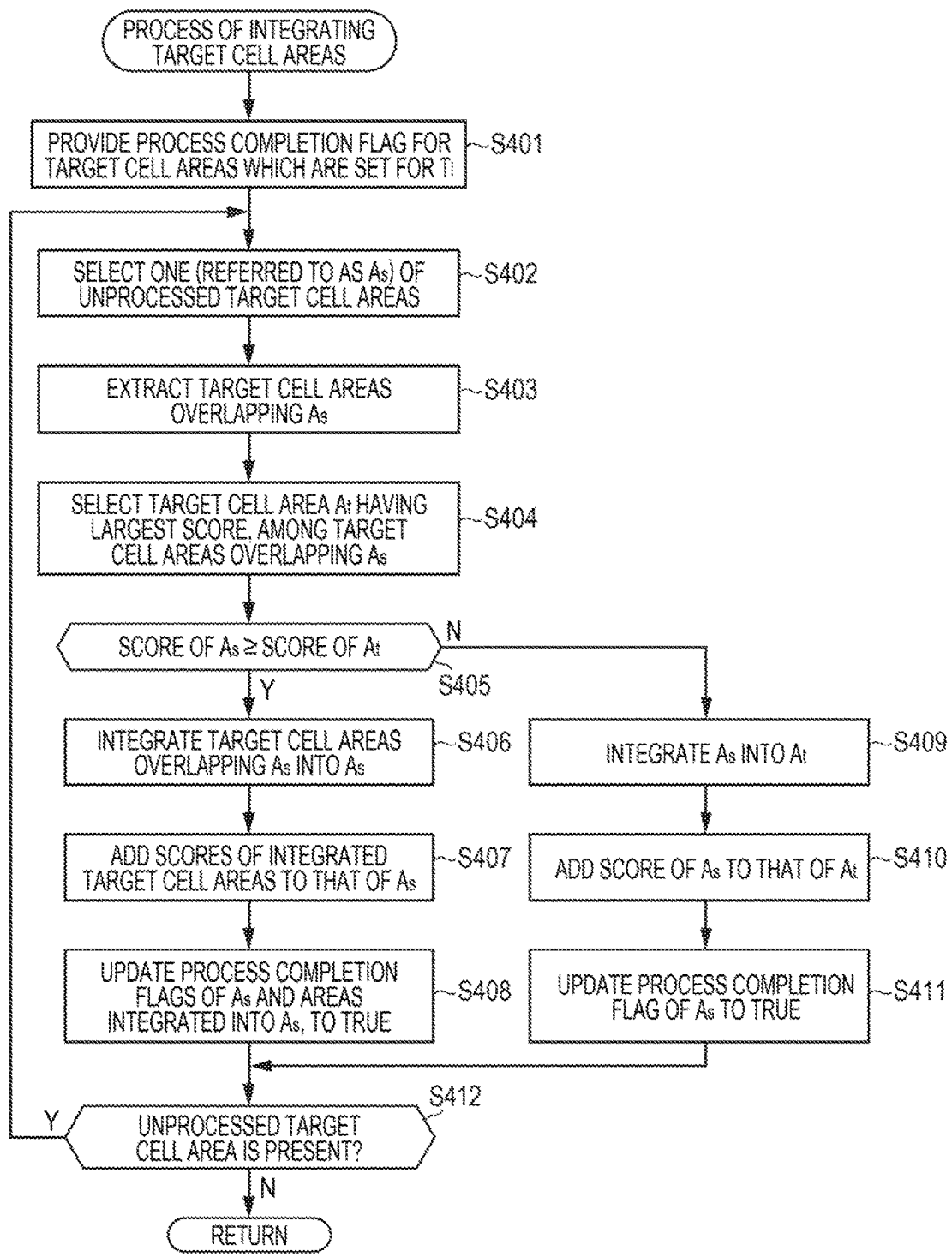
FIG. 8 is a flowchart of a process of integrating target cell areas.

As illustrated in FIG. 8, the image processing apparatus 20 provides a process completion flag for each of the target cell areas which are set for the captured image Ti of the specimen Si (S401). The process completion flag has a true/false value. A value of true (T) indicates that the target cell area has been processed, and a value of false (F)

indicates that the target cell area has not been processed. The initial value of the process completion flag provided in S401 is false (F).

The image processing apparatus 20 selects one of the target cell areas, each of which has a process completion flag indicating that the target cell area has not been processed (S402). The target cell area selected in S402 is referred to as the target cell area As.

The image processing apparatus 20 extracts target cell areas which overlap the target cell area As selected in S402, from the target cell areas which are set for the captured image Ti (S403). The image processing apparatus 20 selects a target cell area having the largest score, from the target cell areas extracted in S403 (S404). The target cell area selected in S404 is referred to as the target cell area At.

If the score of the target cell area As is equal to or larger than that of the target cell area At (S405: Y), the image processing apparatus 20 integrates the target cell areas extracted in S403 into the target cell area As (S406), and adds the scores of the integrated target cell areas to that of the target cell area As (S407). For example, the target cell areas integrated into the target cell area As may be removed, or may be updated so as to have an indication that the target cell areas has been integrated. The image processing apparatus 20 updates the process completion flags of the target cell area As and the target cell areas integrated into the target cell area As, to true (T) (S408).

If the score of the target cell area As is less than that of the target cell area At (S405: N), the image processing apparatus 20 integrates the target cell area As into the target cell area At (S409), and adds the score of the target cell area As to that of the target cell area At (S410). The image processing apparatus 20 updates the process completion flag of the target cell area As to true (T) (S411).

After S408 or S411, if a target cell area which has not been processed is present (S412: Y), the image processing apparatus 20 returns the process back to S402. If no target cell areas which have not been processed are present (S412: N), the image processing apparatus 20 ends the process of integrating target cell areas and causes the process to return.

Back to FIG. 7, the description will be continued. When the image processing apparatus 20 completes the process of integrating target cell areas which are set for the specimen Si, if the variable i does not reach d (the number of specimens to be subjected to the detection or the number of all specimens) (S315: N), the image processing apparatus 20 increments (adds 1 to) i, initializes j and k to 1 (S316), and returns the process back to S302. If the variable i reaches d in S315 (S315: Y), the image processing apparatus 20 causes the process to return.

If the specimen Si is not to be subjected to the detection in S302 (S302: N), and if the variable i does not reach d (S317: N), the image processing apparatus 20 increments (adds 1 to) i, initializes j and k to 1 (S316), and returns the process back to S302. If the variable i reaches d (S317: Y), the image processing apparatus 20 causes the process to return.

3-1-1 (3). Main Process (3)

Back to the flowchart in FIG. 5, the description will be continued. When the image processing apparatus 20 completes the process of detecting target cells for each of the specimens to be processed, the image processing apparatus 20 outputs information about the target cell areas on the basis of the target cell areas after integration for each specimen (S110), and ends the process. For example, the image processing apparatus 20 may sort the target cell areas in descending order of the scores of the target cell areas after integration for each sample, and may display the target cell areas on the display apparatus 60.

According to the process according to the first example described above, parameters used in the detection process may be set on the basis of the estimated target cell count in a sample to be processed and the degree of difficulty in detection of target cells from a sample to be processed.

3-2. Second Example

On the basis of the flowchart in FIG. 9, a process according to a second example which is performed by the image processing system 1 will be described in detail below. The second example is different from the first example in that a detection parameter set is set without using the degree of detection difficulty.

Figure 9:
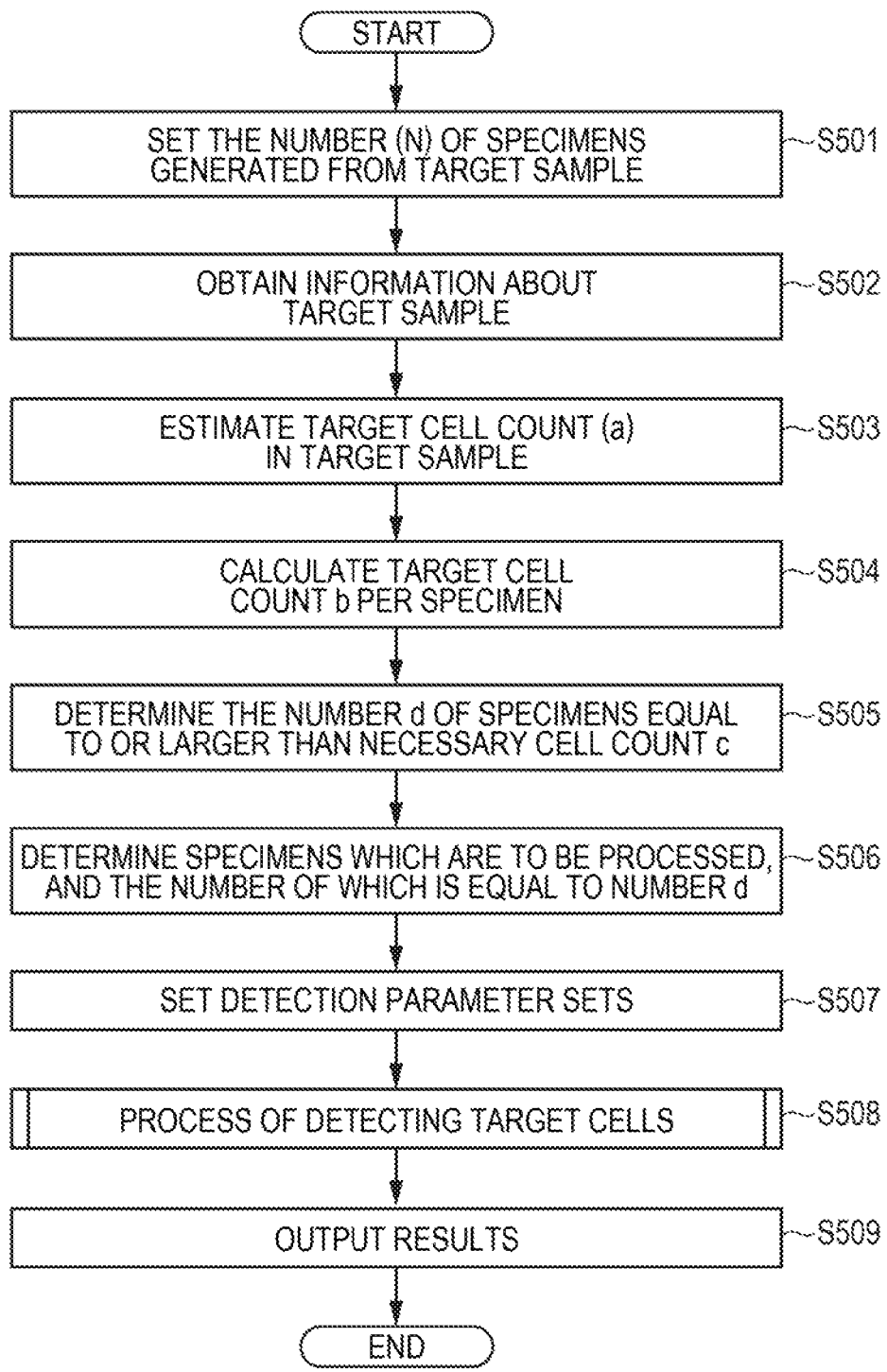
FIG. 9 is a flowchart of a process according to a second example.

As illustrated in FIG. 9, for example, on the basis of data which is input from the input apparatus 50, the image processing apparatus 20 sets the number (N: N is an integer equal to or larger than 1) of specimens generated from a target sample (S501), and obtains information (sample information) about the target sample (S502). The sample information may include at least one of the age, the medical history, and the number of weeks in pregnancy.

The image processing apparatus 20 estimates the target cell count (a) in the target sample on the basis of the sample information obtained in S502 (S503). For example, the image processing apparatus 20 may specify a classification to which the sample information obtained in S502 belongs, and may calculate the estimated target cell count in the sample on the basis of the representative target cell count per unit blood which is predetermined for the specified classification and the blood volume of the test object, i.e., the sample.

The image processing apparatus 20 calculates the target cell count (b) per specimen on the basis of the target cell count (a) calculated in S503 and the number (N) of specimens which is set in S501 (S504). The image processing apparatus 20 determines the number (d) of specimens which are to be subjected to the detection and which contain cell count which is equal to or larger than the necessary cell count (c) necessary for the detection, on the basis of the target cell count (b) per specimen which is calculated in S504 (S505).

The image processing apparatus 20 selects and determines specimens, which are to be processed and the number of which is equal to the number (d), which is determined in S505, of specimens to be subjected to the detection, from the multiple specimens generated from the target sample (S506).

The image processing apparatus 20 sets a detection parameter set on the basis of the information about a specimen which is to be processed and which is determined in S506 and the target cell count (b) per specimen calculated in S504 (S507). For example, the detection parameter set may include the detection target flag indicating whether or not the specimen is to be subjected to the detection, the nucleus-candidate-area parameters indicating a condition of an image area to be extracted as a nucleus candidate area from the specimen, and the determination-target-area parameters indicating a condition of setting determination target areas for an image of the specimen. For example, the image processing apparatus 20 may set the detection target flag on the basis of the information about a specimen which is to be processed and which is determined in S506, and may set the nucleus-candidate-area parameters and the determination-target-area parameters on the basis of a margin (b·d−c) obtained by subtracting the necessary cell count (c) from a value obtained from the expression b·d which indicates multiplication of the number (d) of specimens to be subjected to the detection, by the target cell count per specimen.

The image processing apparatus 20 performs the process of detecting target cells from a sample on the basis of the detection parameter sets which are set in S507 (S508). The process of detecting target cells are described in detail by using the flowchart in FIG. 7, and will not be described since the process is also used in the first example.

When the image processing apparatus 20 completes the process of detecting target cells for each of the specimens to be processed, the image processing apparatus 20 outputs information about the target cell areas on the basis of the target cell areas after integration for each specimen (S509), and ends the process.

According to the process according to the second example described above, parameters used in the detection process may be set on the basis of the estimated target cell count in the sample to be processed.

3-3. Third Example

On the basis of the flowchart in FIG. 10, a process according to a third example which is performed by the image processing system 1 will be described in detail. The third example is different from the first example in that a detection parameter set is set without using the target cell count estimated for a target sample.

Figure 10:
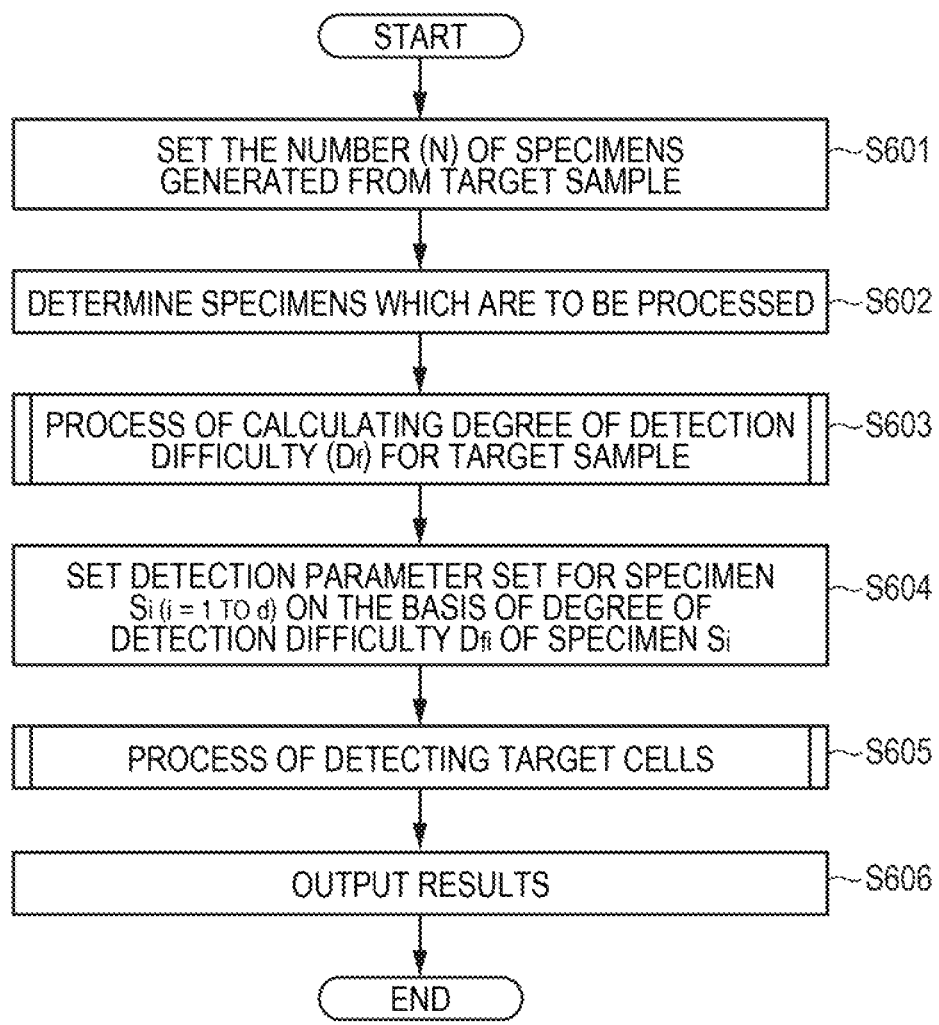
FIG. 10 is a flowchart of a process according to a third example.

As illustrated in FIG. 10, for example, on the basis of data which is input from the input apparatus 50, the image processing apparatus 20 sets the number (N: N is an integer equal to or larger than 1) of specimens generated from a target sample (S601).

The image processing apparatus 20 determines specimens to be processed, from multiple specimens generated from the target sample (S602). For example, the image processing apparatus 20 may set all of the multiple specimens generated from the target sample as specimens to be processed, or may determine specimens to be processed, on the basis of the degree of detection difficulty Df calculated for the target sample. For example, the image processing apparatus 20 may predetermine a ratio in accordance with the range of the degree of detection difficulty (specifically, the higher the degree of detection difficulty is, the larger the ratio is), may determine the number of specimens to be processed, on the basis of a value obtained by multiplying the ratio corresponding to the degree of detection difficulty Df by the number of all specimens (specifically, the value may be an integer by rounding up the obtained multiplication value), and may determine specimens to be processed, on the basis of the determined number of specimens. The number of specimens to be processed is represented by d.

The image processing apparatus 20 performs the process of calculating the degree of detection difficulty which indicates the degree of difficulty in detection of target cells from a specimen to be processed (S603). The process of calculating the degree of detection difficulty is described in detail by using the flowchart in FIG. 6, and will not be described because the process is also used in the first example.

For a specimen Si (i=1 to d) to be processed, the image processing apparatus 20 sets a detection parameter set for the specimen Si on the basis of the degree of detection difficulty Dfi calculated in S603 (S604). For example, the detection parameter set may include the detection target flag indicating whether or not the specimen is to be subjected to the detection, the nucleus-candidate-area parameters indicating a condition of an image area to be extracted as a nucleus candidate area from the specimen, and the determination-target-area parameters indicating a condition of setting determination target areas for an image of the specimen. For example, the image processing apparatus 20 may set the detection target flag on the basis of the information about a specimen which is to be processed and which is determined in S603, and may set the nucleus-candidate-area parameters and the determination-target-area parameters on the basis of the degree of detection difficulty Dfi calculated for the specimen Si.

The image processing apparatus 20 performs the process of detecting target cells from the sample, on the basis of the detection parameter sets which are set in S604 (S605). The process of detecting target cells is described in detail by using the flowchart in FIG. 7, and will not be described because the process is also used in the first example.

When the image processing apparatus 20 completes the process of detecting target cells for each of the specimens to be processed, the image processing apparatus 20 outputs information about the target cell areas on the basis of the target cell areas after integration for each specimen (S606), and ends the process.

According to the process according to the third example described above, the parameters used in the detection process may be set on the basis of the degree of difficulty in detection of target cells from the sample to be processed.

The present invention is not limited to the above-described embodiment. For example, instead of integrating target cell areas, the target cell areas may be displayed in order of their scores. The image processing apparatus 20 does not necessarily obtain a captured image of a sample from the optical microscope 10, and may obtain a captured image of a sample from another computer.

What is claimed is:

1. An image processing apparatus comprising:
    a processor configured to act as:
       a difficulty calculation unit that calculates, for each of a plurality of specimens, a degree of detection difficulty indicating a degree of difficulty in detection of a target cell contained in each of the plurality of specimens, based on a respective test object condition of each of the plurality of specimens;
       a setting unit that sets, for each of the plurality of specimens, a detection parameter on a process of the detection of the target cell from each of a plurality of captured images of the plurality of specimens, based on the degree of detection difficulty, wherein each detection parameter includes information for defining a setting condition for setting determination target areas on which determination as to whether or not the plurality of captured images contains a target cell area is made; and
    a determination unit that makes determination as to whether or not the target cell is contained in the determination target areas which are set based on the detection parameter, on each of the plurality of captured images
    wherein the setting unit sets the setting condition in such a manner that a specimen of the plurality of specimens having a higher degree of detection difficulty is set to have more determination target areas than a specimen of the plurality of specimens having a lower degree of detection difficulty, the higher degree of detection difficulty having a larger value of detection difficulty than a value of the lower degree of detection difficulty.

2. An image processing apparatus comprising:
a processor configured to act as:
   a difficulty calculation unit that calculates a degree of detection difficulty indicating a degree of difficulty in detection of a target cell contained in a specimen, based on a test object condition of each of the specimen;
   a setting unit that sets a detection parameter on a process of the detection of the target cell from a captured image of the specimen, based on the degree of detection difficulty, wherein the detection parameter includes information for defining a setting condition for setting determination target areas on which determination as to whether or not the captured image contains a target cell area is made;
   a determination unit that makes determination as to whether or not the target cell is contained in the determination target areas which are set based on the detection parameter, on the captured image; and
   an integrating unit,
wherein, when a plurality of determination target areas which are determined to contain the target cell and which overlap or match each other are present, the integrating unit integrates the plurality of determination target areas into a determination target area which is determined, by the determination unit, to have a highest probability that the target cell is contained.

3. An image processing apparatus comprising:
a processor configured to act as:
   a difficulty calculation unit that calculates, for each of a plurality of specimens, a degree of detection difficulty indicating a degree of difficulty in detection of a target cell contained in each of the plurality of specimens, based on a respective test object condition of each of the plurality of specimens;
   a setting unit that sets, for each of the plurality of specimens, a detection parameter on a process of the detection of the target cell from each of a plurality of captured images of the plurality of specimens, based on the degree of detection difficulty, wherein each detection parameter includes information for defining a setting condition for setting determination target areas on which determination as to whether or not the plurality of captured images contains a target cell area is made; and
   a determination unit that makes determination as to whether or not the target cell is contained in the determination target areas which are set based on the detection parameter, on each of the plurality of captured images
wherein the difficulty calculation unit calculates so that:
(i) the degree of detection difficulty corresponding to a specimen of the plurality of specimens having a higher degree of evenness of thickness has a lower value than a degree of detection difficulty corresponding to a specimen of the plurality of specimens having a lower degree of evenness of thickness, wherein the higher degree of evenness of thickness is better evenness than the lower degree of evenness of thickness,
(ii) the degree of detection difficulty corresponding to a specimen of the plurality of specimens having a lower degree of brightness of a nucleus contained in the specimen has a lower value than a degree of detection difficulty corresponding to a specimen of the plurality of specimens having a higher degree of brightness of a nucleus contained in the specimen, wherein the lower degree of brightness is a smaller brightness than the higher degree of brightness, and
(iii) the degree of detection difficulty corresponding to a specimen of the plurality of specimens having a higher ratio of pixels which are contained in the specimen and whose density is lower than a predetermined density has a has a higher value than a degree of detection difficulty corresponding to a specimen of the plurality of specimens having a lower ratio of pixels which are contained in the specimen and whose density is lower than a predetermined density, wherein the lower ratio of pixels which are contained in the specimen and whose density is lower than the predetermined density is lower than the higher ratio of pixels which are contained in the specimen and whose density is lower than the predetermined density.

4. The image processing apparatus according to claim 1, wherein each of the detection parameters includes information for determining whether or not each of the plurality of specimens generated from a target sample is to be subjected to detection of the target cell in each of the plurality of specimens, and
the setting unit sets information about each of the specimens to be subjected to the detection, among the plurality of specimens generated from the target sample, based on each of the degree of detection difficulties.

5. A non-transitory computer-readable storage medium storing a program for causing the image processing apparatus according to claim 1 to be a computer that functions as:
the difficulty calculation unit;
the setting unit; and
the determination unit.

6. An image processing method using the image processing apparatus according to claim 1, the method comprising:
calculating, for each of the plurality of specimens, the degree of detection difficulty;
setting, for each of the plurality of specimens, the detection parameter; and
determining as to whether or not the target cell is contained in the determination target areas which are set based on the detection parameter, on each of the plurality of captured images.

7. The image processing apparatus according to claim 2, wherein the detection parameter includes information for determining whether or not each of a plurality of specimens generated from a target sample is to be subjected to detection of the target cell in the specimen, and
the setting unit sets information about the specimen to be subjected to the detection, among the plurality of specimens generated from the target sample, based on the degree of detection difficulty.

8. A non-transitory computer-readable storage medium storing a program for causing the image processing apparatus according to claim 2 to be a computer that functions as:
the difficulty calculation unit;
the setting unit;
the determination unit; and
the integrating unit.

9. An image processing method using the image processing apparatus according to claim 2, the method comprising:
calculating the degree of detection difficulty;
setting the detection parameter; and determining as to whether or not the target cell is contained in the determination target areas which are set based on the detection parameter.

10. The image processing apparatus according to claim 3, wherein each of the detection parameters includes information for determining whether or not each of the plurality of specimens generated from a target sample is to be subjected to detection of the target cell in each of the plurality of specimens, and the setting unit sets information about each of the specimens to be subjected to the detection, among the plurality of specimens generated from the target sample, based on each of the degree of detection difficulties.

11. A non-transitory computer-readable storage medium storing a program for causing the image processing apparatus according to claim 3 to be a computer that functions as:

the difficulty calculation unit;

the setting unit; and the determination unit.

12. An image processing method using the image processing apparatus according to claim 3, the method comprising:

calculating, for each of the plurality of specimens, the degree of detection difficulty;

setting, for each of the plurality of specimens, the detection parameter; and determining as to whether or not the target cell is contained in the determination target areas which are set based on the detection parameter, on each of the plurality of captured images.

* * * * *